(12) United States Patent
Ulrich et al.

(10) Patent No.: US 8,105,605 B2
(45) Date of Patent: *Jan. 31, 2012

(54) ALLERGEN FORMULATION

(75) Inventors: Jorj Terry Ulrich, Corvallis, MT (US); Alan Worland Wheeler, Horsham (GB)

(73) Assignee: Allergy Therapeutics (UK) Ltd., Worthing, West Sussex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/749,326

(22) Filed: Mar. 29, 2010

(65) Prior Publication Data

US 2010/0183659 A1   Jul. 22, 2010

Related U.S. Application Data

(60) Continuation of application No. 11/040,952, filed on Jan. 21, 2005, now Pat. No. 7,718,178, which is a division of application No. 09/402,273, filed as application No. PCT/EP98/02138 on Apr. 3, 1998, now abandoned.

(30) Foreign Application Priority Data

Apr. 5, 1997   (GB) .................................. 9706957.9

(51) Int. Cl.
- A61K 38/00    (2006.01)
- A61K 39/00    (2006.01)
- A61K 39/35    (2006.01)
- A61K 39/36    (2006.01)

(52) U.S. Cl. ..................... 424/185.1; 424/275.1; 514/1.1
(58) Field of Classification Search .......................... None
See application file for complete search history.

(56) References Cited

U.S. PATENT DOCUMENTS

| | | | |
|---|---|---|---|
| 3,541,201 A | 11/1970 | Brown et al. | |
| 3,792,159 A | 2/1974 | Green et al. | |
| 4,070,455 A | 1/1978 | Green et al. | |
| 4,258,029 A | 3/1981 | Moloney et al. | |
| 4,912,094 A | 3/1990 | Myers et al. | |
| 4,956,489 A | 9/1990 | Auriol et al. | |
| 4,987,237 A | 1/1991 | Myers et al. | |
| 5,244,663 A | 9/1993 | Bruttmann et al. | |
| 5,750,110 A | 5/1998 | Prieels et al. | |
| 5,762,943 A | 6/1998 | Dolovich et al. | |
| 5,776,468 A | 7/1998 | Hauser et al. | |
| 5,795,862 A | 8/1998 | Frank et al. | |
| 5,973,128 A | 10/1999 | Lingwood et al. | |
| 5,997,873 A | 12/1999 | Srivastava | |
| 6,146,632 A | 11/2000 | Momin et al. | |
| 7,718,178 B2 * | 5/2010 | Ulrich et al. ................ | 424/185.1 |
| 2003/0007977 A1 | 1/2003 | Wheeler et al. | |
| 2003/0165512 A1 | 9/2003 | Wheeler et al. | |

FOREIGN PATENT DOCUMENTS

| | | |
|---|---|---|
| EP | 0239400 | 8/1994 |
| EP | 0640347 | 3/1995 |
| EP | 0182442 | 4/1996 |
| EP | 0988862 | 6/2001 |
| EP | 1031347 | 4/2002 |
| GB | 1128637 | 9/1968 |
| GB | 1377074 | 12/1974 |
| GB | 1492973 | 11/1977 |
| GB | 2220211 | 1/1990 |
| WO | 98/43670 | 10/1988 |
| WO | 92/16556 | 10/1992 |
| WO | 94/27636 | 12/1994 |
| WO | 95/05850 | 3/1995 |
| WO | 95/17209 | 6/1995 |
| WO | 96/25664 | 8/1996 |
| WO | 96/34626 | 11/1996 |
| WO | 98/58956 | 12/1998 |
| WO | 99/10375 | 3/1999 |
| WO | 99/16884 | 4/1999 |
| WO | 99/24577 | 5/1999 |
| WO | 99/64067 | 12/1999 |
| WO | 99/66043 | 12/1999 |
| WO | 00/29582 | 5/2000 |
| WO | 00/50078 | 8/2000 |
| WO | 00/62801 | 10/2000 |
| WO | 00/65058 | 11/2000 |
| WO | 00/72876 | 12/2000 |
| WO | 00/78353 | 12/2000 |
| WO | 01/29214 | 4/2001 |
| WO | 01/51082 | 7/2001 |

OTHER PUBLICATIONS

Hertl et al. 'Immunologic mechanisms in hypersensitivity reactions to metal ions: an overview,' Allergy. 55:108-115, 2000.*
Gonzalez-Hernandex et al. 'Peripheral Blood CD161+ T cells from Asthmatic Patients are Activated During Asthma Attack and Predominantly Produce IFN-gamma.' Scand. J. Immunol. 65:368-375, 2007.*
Mamessier et al. 'Cytokines in atopic diseases: revisiting the Th2 dogma.' Eur. J. Dermatol. 16(2):103-113, 2006.*
Yssel et al. 'Regulatory T cells and allergic asthma.' Microbes and Infection 899-904, 2001.*
Yang et al., Mechanisms of Monophosphoryl Lipid A Augmentation of Host Responses to Recombinant HagB from Porphyromonas Gingivalis, Infection and Immunity 70(7):3557-3565 (2002). Zhou et al., Comparison of Enzyme Activities of Tissues Lining Portals of Absorption of Drugs Species Differences, Int'l J. Pharmaceutics 70(3):271-283 (1991) (Biosis Abstract).
MPL Structure page, taken from Hopkins et al., Allergol et Immunopathol 29(6):245-254 (2001).
Ribi Adjuvant Fact Sheet (2003).
Akahira-Azuma et al., Early Delayed-Type Hypersensitivity Eosinophil Infiltrates Depend on T Helper 2 Cytokines and Interferon-Gamma via CXCR3 Chemokines, Immunology 111:306-317 (2004).
Chauncey et al., Enzymes of Human Saliva, The Determination, Distribution, and Origin of Whole Saliva Enzymes, J. Dental Res., 33(3):321-334 (1954).
Chauncey, Salivary Enzymes, J. Am. Dental Assoc., 63:42-50 (1961).
Cleland et al., The Development of Stable Protein Formulations: A Close Look at Protein Aggregation, Deamidation and Oxidation, Critical Reviews in Therapeutic Drug Carrier Systems 10(4):307-377 (1993).
Cox et al., Adjuvants-A Classification and Review of their Modes of Action Vaccine 15(3): 248-256 (1997).

(Continued)

*Primary Examiner* — Nora Rooney
(74) *Attorney, Agent, or Firm* — Karen Canaan; CanaanLaw, P.C.

(57) ABSTRACT

Provided is a pharmaceutical composition comprising tyrosine, an optionally modified allergen, and 3-DMPL, which is useful in the prevention and treatment of allergies.

8 Claims, No Drawings

OTHER PUBLICATIONS

Dalton et al., The Solubilities of Certain Amino Acids in Water, the Densities of Their Solutions At Twenty-five Degrees, and The Calculated Heats of Solution and Partial Molal Volumes, J. Biol. Chem. 103(2):549-576 (1933).

Dearman et al., Divergent Antibody Isotype Responses Induced in Mice by Systemic Exposure to Proteins: a Comparison of Ovalbumin with Bovine Albumin, Food and Chemical Toxicology 38:351-360 (2000).

Dehlink et al., Absence of Systemic Immunologic Changes During Dose Build-up Phase and Early Maintenance Period in Effective Specific Sublingual Immunotherapy in Children, Clinical and Experimental Allergy 36:32-39 (2006).

Drachenberg et al., A Well-Tolerated Grass Pollen-Specific Allergy Vaccine Containing a Novel Adjuvant, Monophosphoryl Lipid A, Reduces Allergic Symptoms after only Four Preseasonal Injections, Allergy 498-505 (2001).

Drachenberg et al., Short-Term Immunotherapy with Tree Pollen Allergoids and the Adjuvant Monophosphoryl A—Results from a Multi-Centre, Placebo-Controlled Randomised, Double-Blind Study, Allergologie 25(9):466-474 (2002).

Drachenberg et al., Short-Term Immunotherapy Using an Allergy Vaccine Adjuvanted with Monophosphoryl Lipid A: A Post-Marketing Surveillance Study, Int. Rev. Allergol. Clin. Immunol. 8(4):219-223 (2002).

Drachenberg et al., Efficacy and Tolerability of Short-Term Specific Immunotherapy with Pollen Allergoids Adjuvanted by Monophosphoryl Lipid A (MPL) for Children and Adolescents, Allergol et Immunopathol 31 (5):270-277 (2003).

Dunn et al., The Solubility of the Amino Acids in Water, J. Biol. Chem. 103(2):579-595 (1933).

Garren et al., Buccal Drug Absorption. I. Comparative Levels of Esterase and Peptidase Activities in Rat and Hamster Buccal and Intestinal Homogenates, Int'l J. Pharmaceutics 48:189-194 (1988).

Holen et al., Specific T Cell Lines for Obalbumin, Ovomucoid, lysozyme and Two OA Synthetic Epitopes, Generated from Egg Allergic Patients PBMC Clin. Exp. Allergy 26: 1080-1088 Abstract (1996).

Hoyne et al., Peptide-Medicated Regulation of the Allergic Immune Response Immunology and Cell Biology 74: 180-186 (1996).

Jackson et al., Reduction of Human Anti-Tetanus Toxoid Antibody in hu-PBL-SCID mice by Immunodominant Peptides of Tetanus Toxoid, Clin Exp Immunol 137:245-252 (2004).

Johansen et al., Immunogenicity and Protective Efficacy of a Formalin-Inactivated Rotavirus Vaccine Combined with Lipid Adjuvants, Vaccine 21:368-375 (2003).

Lindquist et al., Esterases in Human Saliva, Enzyme 20:277-291 (1975).

Lindquist et al., Origin of Esterases in Human Whole Saliva, Enzyme 22:166-175 (1977).

McCluskie et al., CpG DNA is an Effective Oral Adjuvant to Protein Antigens in Mice, Vaccine 19:950-957 (2001).

Marsh et al., Studies on "Allergoids" Prepared from Naturally Occurring Allergens, Immunology 18:705-722 (1970).

March et al., Preparation and Properties of "Allergoids" Derived from Native Pollen Allergens by Mild Formalationi Treatment Int. Arch. Allergy 41:199-215 (1971).

Moran et al., Chemical Modification of Crude Timothy Grass Extract (III) The Effect of Glutaraldehyde Induced Aggregation on Antigenic and Immunogenic Properties, Int. Ach. Allergy Appl. Immunol. 55:315-321 (1977).

Ngo et al., The Protein Folding Problem and Tertiary Structure Prediction, Mertz, Jr. et al. Eds. Birkhauser Boston, pp. 491-495 (1994).

Nixon-George et al., The Adjuvant Effect of Stearyl Tyrosine on a Recombinant Subunit Hepatitis B Surface Antigen J. Immunol 144(12): 4798-4802 (1990).

Pajno et al., Clinical and Immunologic Effects of Long-term Sublingual Immunotherapy in Asthmatic Children Sensitized to Mites: A Double-Blind, Placebo-Controlled Study, Allergy 55:842-849 (2000).

Patel et al., Pollinex Quattro: A Novel and Well-Tolerated, Ultra Short-Course Allergy Vaccine, Expert. Rev. Vaccines 5(5):617-629 (2006).

Patterson et al., Polymerized Ragweed Antigen E(I) Preparation and Immunological Studies, J. Immun. 110:1402-1412 (1973).

Patterson et al., Polymerized Ragweed Antigen E(II) Preparation and Immunological Studies, J. Immun. 110:1413-1418 (1973).

Patterson et al., Polymerized Ragweed Antigen E(III) Preparation and Immunological Studies, J. Immun. 112:1855-1860 (1974).

Penny et al., Further Studies on the Adjuvanticity of Stearyl Tyrosine and Ester Analogues Vaccine 11:1129-1134 (1993).

Sasaki et al., Comparison of Intranasal and Intramuscular Immunization Against Human Immunodeficiency Virus Type 1 with a DNA-Monophosphoryl Lipid A Adjuvant Vaccine Infect. Immun. 66(2): 823-826 (1998).

Scalzo et al. Induction of Protective Cytotoxic T Cells to Murine Cytomegalovirus by Using a Nonapedtide and a Human-Compatible Ajduvant J. Virol 69(2): 1306-1309 (1995).

Schneerson et al., Evaluation of Monophosphoryl Lipid a MPL as an Adjuvant Enhancement of the Serum Antibody Response in Mice to Polysaccharide-Protein Conjugates by Concurrent Injection with MPL J Immunol 147:2136-2140 (1991).

Sri-Ram, Chemical Modification of Proteins and Their Significance in Enzymology, Immunochemistry, and Related Subjects, Advances in Enzymology: and Related Subjects of Biochemistry 24:105-160 F.F. Nord, ed., John Wiley & Sons, (1962).

Stuck et al., Short-Term Preseasonal Immunotherapy with Birch Pollen Allergoid Plus Monosphosphorylipid a (MPL): Influence on Cytokine Production of Peripheral T Cells in Patients with Allergic Rhinitis, Allergy Clin Immunol Int—J World Allergy Org 16(2):60-64 (2004).

Tan et al., Human Saliva Esterases: Genetic Studies, Hum. Heredity 26:207-216 (1976).

Ulrich et al., Monophosphoryl Lipid A as an Adjuvant: Past Experience and New Directions, Vaccine Design: The Subunit and Adjuvant Approach Powell & Newman, eds., Plenum Press, N. Y. (1995).

Valdez et al., Interactions of the Salivary and Gastronintestinal System I. The Role of Saliva in Digestion, Digestive Diseases 9(9):125-132 (1991).

Van Ginkel et al., Vaccines for Mucosal Immunity to Combat Emerging Diseases, Emerging Infectious Diseases, Emerging Infectious Diseases 6(2):123-132 (2000).

Verhoef et al., Transport of Peptide and Protein Drugs Across Biological Membranes, Eur J. Drug Met. Pharm. 15(2): 83-93 (1990).

Vogel et al., Drug Discovery and Evaluation, Pharmacological Assays pp. 440-444 (1996).

Vourdas et al., Double-blind, Placebo-Controlled Evaluation of Sublingual Immunotherapy with Standardized Olive Pollen Extract in Pediatric Patients with Allergic Rhinoconjuntivitis and Mild Asthma Due to Olive Pollen Sensitization, Allergy 53:662-672 (1998).

Wheeler et al., L-Tyrosine as an Immunological Adjuvant, Int. Archs Allergy Appl. Immun 69:113-119 (1982).

Wheeler et al., Chemical Modification of Crude Timothy Grass Extract (II) Class and Specificity of Antibodies Induced by Chemically Modified Timothy Grass Pollen Extract, Int. Ach. Allergy Appl. Immunol. 50:709-728 (1976).

Wheeler et al., A Th1-Inducing Adjuvant, MPL®, Enchaces Antibody Profiles in Experimental Animals Suggesting it has the Potential to Improve the Efficacy of Allergy Vaccines, Intl. Arch. Allergy Immunol. 126:135-139 (2001).

* cited by examiner

ALLERGEN FORMULATION

CROSS-REFERENCE TO RELATED APPLICATIONS

This application is a continuation of U.S. patent application Ser. No. 11/040,952, filed on Jan. 21, 2005, now U.S. Pat. No. 7,718,178, which is a divisional of U.S. patent application Ser. No. 09/402,273, filed on Dec. 13, 1999, now abandoned, which claimed the benefit under 35 U.S.C. §365 to PCT/EP1998/002138, filed on Apr. 3, 1998, which claimed priority to UK Application No. 9706957.9, filed on Apr. 5, 1997.

TECHNICAL FIELD

This invention relates to novel formulations for use in desensitization therapy of allergy sufferers.

BACKGROUND OF THE INVENTION

It is known that desensitization therapy results in a changed immunological response specific for the allergens administered. Such changes are considered to be responsible for the beneficial effects of the treatment and amelioration of the symptoms of allergy.

The immunological changes responsible for benefit are not entirely understood. Although a raised allergen specific IgG antibody response is considered to be a desirable outcome of therapy, it is now believed that certain changes in the allergen specific T cell (i.e., T lymphocyte) response are more important.

Two subclasses of T cell, TH1-like and TH2-like interact with one another via various messenger molecules. In an allergic subject it appears that there is a greater allergen specific TH2 than a TH1 activity. This can lead to a high allergen specific IgE antibody level and greater eosinophil activity. These are two important components of the allergic syndrome.

A change in the above situation to one where there is greater allergen specific TH1 rather than TH2 activity is thought to be an important component of immunotherapy leading to a clinical benefit.

GB-A-1 377 074, corresponding to U.S. Pat. No. 3,792,159, describes a process for preparing coprecipitates of tyrosine having an allergen dispersed therein.

GB-A-1 492 973, corresponding to U.S. Pat. No. 4,070,455, describes a process for preparing coprecipitates of tyrosine having a modified allergen dispersed therein. The allergen is modified by treatment with an agent, such as glutaraldehyde, which causes intra-molecular cross-linking and reduces the allergenicity of the product relative to the unmodified allergen.

3 de-O-acylated monophosphoryl lipid A (hereinafter "3-DMPL" or "MPL") is known from GB-A-2 220 211, corresponding to U.S. Pat. No. 4,912,094, and assigned to Ribi Immunochem Research, Inc. (Hamilton, Mont.) ("Ribi"). Chemically it is a mixture of 3 de-O-acylated monophosphoryl lipid A with 4, 5, or 6 acylated chains and is manufactured by Ribi. A preferred form of 3 de-O-acylated monophosphoryl lipid A is disclosed in International Patent Publication No. WO 92/116556. 3-DMPL is an example of a substance that can enhance the TH1 over TH2 directing properties of administered allergens.

SUMMARY OF THE INVENTION

According to the present invention there is provided a pharmaceutical composition comprising tyrosine, an optionally modified allergen, and 3-DMPL. Typically, the allergen is coated with and/or adsorbed onto tyrosine, for example by co-precipitation or mixing.

The 3-DMPL can be mixed with the other components of the composition prior to administration. Alternatively, it can be formulated together with the other components during manufacture of the product. Alternatively, it can be administered at a different site or time than the other components. Administration can be by a number of routes including parenteral and enteral.

A further aspect of the invention thus provides a method of treating a patient who is susceptible to allergy, which method comprises administering to the said patient an effective amount of tyrosine, an optionally modified allergen, and 3-DMPL.

A further aspect of the invention provides use of tyrosine, an optionally modified allergen, and 3-DMPL, in the preparation of a medicament for use in the prevention or treatment of allergy.

The allergen may be derived from any allergy causing substance, such as a pollen (e.g., ragweed or birch pollen), food, insect venom, mould, animal fur, or house dust mite (*D. farinae* or *D. pteronyssinus*). As used herein, "allergen" includes a mixture of allergens, which may be from a single source or more than one source. The term "allergen" also includes peptides containing one or more epitopes of an allergen, such as allergen fragments, prepared by total synthesis, by enzymatic degradation of allergens, or by other means.

The allergen is optionally modified by reaction with a cross-linking agent such as a dialdehyde, more particularly glutaraldehyde.

A further aspect of the invention provides a process for the preparation of a pharmaceutical composition in accordance with the invention, which process comprises: (a) optionally modifying an allergen by reaction with a cross-linking agent; (b) mixing an aqueous solution of the optionally modified allergen with a solution of tyrosine in a strong aqueous acid; (c) neutralizing the mixture of solutions, thereby co-precipitating tyrosine and modified allergen; (d) mixing the product with 3-DMPL; and (e) optionally, adding a physiologically acceptable carrier.

Suitable physiologically acceptable carriers include phenol-saline and sterile water.

DETAILED DESCRIPTION OF THE INVENTION

Typically, the allergen is modified by treatment with a dialdehyde such as glutaraldehyde, in aqueous solution at a pH of between 5 and 10, typically about 7, and a temperature of between 0° C. and 100° C., more usually between 4° C. and 37° C. for up to 10 hours, for example about two hours at room temperature. The ratio of allergen to glutaraldehyde is typically in the range 50:1 to 2:1, for example about 10:1.

The intermediate can be freeze dried or used in the next stage.

A solution of the modified allergen, typically at pH 7±1, obtained either as the reaction mixture from the cross-linking process or from the solvation of a solid, is then mixed with a solution of tyrosine in a strong aqueous acid. The strong acid is usually an inorganic acid, preferably hydrochloric acid. The solution of allergen used in this step typically contains between 0.1 µg/mL and 1000 µg/mL allergen protein, for example about 400 µg/mL. The ratio of allergen:tyrosine in the mixture is typically in the range 1:4×10$^5$ to 1:1×10$_2$ w/w.

The resulting mixture of solutions of allergen and tyrosine is neutralized. By neutralization is meant an adjustment of pH to a value within the range 4.0 to 7.5. It is important that, at no time, or at least at no prolonged time, during the neutralization does the pH of the solution rise appreciably above 7.5. This condition can be met by vigorous stirring of the solution and by the use only of the required amount of base, if desired. Various buffering agents can usefully be added to the solutions of allergen to assist in pH control during the mixing and neutralizing stages.

A particularly useful method of carrying out the neutralization is for separate streams of the solution of tyrosine in acid and the neutralizing base to be run into the solution of allergen. The rates of flow of the added solutions are controlled by pH-state, that is, by equipment that regulates the flow of one or both of the solutions so that the pH of the reaction mixture remains substantially constant at a predetermined level. We have found that optimum results are usually obtained by pH control within the range 6.5 to 7.5 though the precise pH may vary according to the nature of the allergen.

The result of the neutralization is the immediate precipitation of the tyrosine, within and/or upon which the solution of allergen is occluded and/or adsorbed. After the precipitation the mixture is either washed immediately or allowed to stand for a period of from a few hours to a day or two prior to washing.

The resulting precipitate may be removed from the solution by centrifugation or filtration and washed, e.g., with phenol-saline, before being resuspended in a physiologically acceptable carrier such as phenol-saline, or sterile water, to produce an injectable composition suitable for use in desensitization therapy in combination with 3-DMPL.

MPL that has been dissolved by the method described in Preparation 3 below or by sonication can be diluted by various means prior to its addition to tyrosine adsorbates of allergens or modified allergens. The preparation of MPL is initially made at a concentration of typically between 0.5 mg/mL and 4 mg/mL, for example 1 mg per mL. It can then be diluted to a concentration of between 500 µg/mL and 20 µg/mL, preferably about 100 µg/mL. This dilution can be made in pure water, or in an aqueous glycerol solution containing between 1% and 4%, preferably 2%, glycerol. Such dilutions can then be added to a suspension of the tyrosine adsorbate prepared as described above. For convenience, the concentration of the MPL solution and the tyrosine adsorbate suspension, respectively, may be selected such that approximately equal volumes of each are admixed to obtain the final product for injection. A typical final product contains about 100 µg/mL of allergen and about 250 µg/mL of MPL.

The following Example illustrates the present invention:

Preparation 1

A neutral solution of approximately 0.5 mg/mL grass pollen extract which had been partially purified by dialysis or fractionation was chemically modified by the addition of an equal volume of 0.25% w/v glutaraldehyde and the mixture stirred for approximately 2 hours at room temperature. To the above mixture was added phosphate buffer solution at a pH of 7±1. The allergen solution was co-precipitated with tyrosine by the simultaneous addition of one volume of L-tyrosine in HCl (prepared by dissolving 24 g L-tyrosine to 100 mL with 3.8M HCl) and one volume of 3.2M NaOH, to four volumes of allergen solution, with vigorous agitation. The suspension so formed was centrifuged, washed repeatedly with buffered saline to remove contaminants and resuspended to the original volume in buffered saline pH 6±1.

3-DMPL suitable for coadministration with the above formulation was prepared as described in Preparation 3 below.

Preparation 2

Eight mg of ovalbumin (XOA) were dissolved by mixing in 20 mL of EVANS solution. Next, 6.9 mL of phosphate buffer were added with mixing. The solution was placed in a 100 mL beaker containing a magnetic stir bar. While mixing using a magnetic stirrer, 6.9 mL of 3.2N NaOH and 6.9 mL of 3.8N HCL containing 24% w/v tyrosine were added simultaneously, dropwise, over a period of 5 min to form a precipitate. The mixture was allowed to stir for an additional 5 min and then transferred to a 50 mL centrifuge tube and centrifuged for 10 min at 2500 rpm. After centrifugation, the supernatant was decanted and the pelleted precipitate resuspended in 40 mL of phosphate buffer. The mixture was centrifuged for 5 min at 2500 rpm. After centrifugation, the supernatant was decanted and the precipitate resuspended in 40 mL of phosphate buffer. The mixture was centrifuged for 5 min at 2500 rpm. After centrifugation, the supernatant was decanted and the pelleted precipitate resuspended in 40 mL of phosphate buffered saline, pH 7.2, containing 0.4% v/v glycerol and 0.01% w/v thimerosal as a preservative. The final product contained approximately 40 mg/mL of tyrosine adsorbate. Assuming 100% binding of the XOA to the tyrosine adsorbate, the XAO was at 200 µg/mL in the final product. The XOA-tyrosine adsorbate was stored at 4° C. until needed.

Preparation 3

A 4 mg/mL solution of 1,2-dipalmitoyl-SN-glycero-3-phosphocholine ("DPPC") in absolute ethanol was prepared. For each 1 mg of MPL®-TEA salt to be solubilized, 27 µl of DPPC was added to dissolve the MPL®. The ethanol was removed by blowing a stream of $N_2$ gently into the vial. Next 1 mL of pyrogen-free water for injection was added for each mg of MPL® in the dried MPL®/DPPC mixture. The solution was sonicated in a bath sonicator at 60-70° C. until clear. The MPL®/DPPC solution was then filter sterilized by filtration through a SFCA 290-4520 Nalgene 0.2 µm filter. The MPL®/DPPC solution was aseptically dispensed at 1 mg/mL into depyrogenated vials, labelled MPL®-AF, and stored at 4° C.

Biological Activity

TH1 inducing activity in mice can be equated with the production of IgG2a and IgG2b antibodies and the TH2 inducing activity with the production of IgG 1 antibodies and IgE antibodies.

Therefore, as an example, an experiment was carried out in mice to demonstrate the profiles of the allergen specific antibodies to an exemplar allergen ovalbumin (XOA), which is a well-known food allergen derived from chicken eggs. It was confirmed that a formulation consisting of MPL+XOA+tyrosine stimulated a more advantageous antibody profile than MPL+XOA, XOA+tyrosine, or XOA alone.

Groups of 8 BALB/c female mice, 6-8 weeks of age, were injected subcutaneously in the inguinal area with 0.2 mL of one of the following vaccines:

XOA+Tyrosine: The XOA tyrosine adsorbate prepared in Preparation 2 above was diluted with an equal volume of phosphate buffered saline within 30 min prior to injection.

XOA+Tyrosine+MPL: The XOA tyrosine adsorbate prepared in Preparation 2 above was diluted with an equal volume of MPL®-AF at 500 μg/mL in phosphate buffered saline within 30 min prior to injection.

XOA+MPL: XOA was dissolved in phosphate buffered saline at 200 μg/mL and diluted with an equal volume of MPL®-AF at 500 μg/mL in phosphate buffered saline within 30 min prior to injection.

XOA Alone: XOA was dissolved at 200 μg/mL in phosphate buffered saline and diluted with an equal volume of phosphate buffered saline.

Twenty-one days later the four groups of mice were boosted with 0.2 mL of freshly prepared vaccines. Fourteen days following the booster the mice were bled and the sera separated and stored at −70° C. until assay.

The sera were assayed by conventional ELISA technique using horseradish conjugated goat anti-mouse IgG1, IgG2a, and IgG2b antibodies purchased from Southern Biotechnology, Inc. (Birmingham, Ala.) and used according to the manufacturer's instruction. The IgG1, IgG2a, and IgG2b titers represent the reciprocal serum dilution giving a reading of >0.1 OD units at $A_{490}$. The serum IgE levels were measured using an anti-IgE capture ELISA followed by the use of a biotinylated ovalbumin probe. Binding was measured following the addition of a horseradish conjugated strepavidin preparation. The results are reported in Table 1 as OD units at $A_{490}$.

TABLE 1

| Formulation | $IgG_1$ | $IgG_{2a}$ Titer | $IgG_{2b}$ Titer | IgE OD at 1/10 Dilution |
|---|---|---|---|---|
| XOA + Tyrosine | 102400 | 100 | 200 | 0.213 |
| XOA + Tyrosine + MPL | 409600 | 102400 | 102400 | 0.104 |
| XOA + MPL | 102400 | 200 | 400 | 0.218 |
| XOA Alone | 6400 | <100 | <100 | 0.235 |
| Normal Mouse Serum Values | <100 | <100 | <100 | 0.095 |

Of particular important is the fact that the combination of allergen+tyrosine+MPL induces less allergen specific IgE antibody than the other combinations. Furthermore, the ratio of IgG2a or IgG2b to IgG1 antibodies is greater and consistent with the highest levels of the two former antibody isotypes seen in the experiment in the mice given allergen+tyrosine+MPL than in any other group of mice. This is indicative of a better ratio of the TH1 cell induction over the TH2 cell induction in this group compared with that induced in the other groups of mice.

We claim:

1. A method of treating a patient who is susceptible to allergy caused by a house dust mite allergen, comprising administering to the patient an effective amount of a composition comprising tyrosine, a glutaraldehyde modified house dust mite allergen, and 3-de-O-acylated monophosphoryl lipid A (3-DMPL or MPL), wherein the house dust mite is selected from *D. farinae* and *D. pteronyssinus*.

2. The method of claim 1, wherein the composition is administered to the patient in a single pharmaceutical formulation.

3. The method of claim 2, wherein the single pharmaceutical formulation is administered to the patient as an injectable composition.

4. The method of claim 3, wherein the injectable composition is administered to the patient parenterally or enterally.

5. The method of claim 2, wherein the allergen is adsorbed onto the tyrosine.

6. The method of claim 1, wherein administration of the composition results in increased IgG antibody titers.

7. The method of claim 6, wherein the IgG antibodies are selected from the group consisting of IgG1, IgG2a, and IgG2b.

8. The method of claim 1, wherein administration of the composition results in normal IgE levels.

* * * * *